United States Patent [19]
Kudo et al.

[11] Patent Number: 6,080,720
[45] Date of Patent: *Jun. 27, 2000

[54] TREATMENT METHOD OF BONE AND OSTEOBLASTS WITH NEUROTROPHIN-3 (NT-3)

[75] Inventors: Akira Kudo, Kodairo; Tohru Nakanishi; Masaharu Takigawa, both of Okayama, all of Japan

[73] Assignee: Hoechst Japan Limited, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/505,539

[22] Filed: Jul. 21, 1995

[30] Foreign Application Priority Data

Jul. 22, 1994 [JP] Japan .................................. 6-201257

[51] Int. Cl.$^7$ .................................................... A61K 38/18
[52] U.S. Cl. .................................................. 514/12; 514/2
[58] Field of Search .......................................... 514/2, 12

[56] References Cited

FOREIGN PATENT DOCUMENTS

91/03569  3/1991  WIPO .

OTHER PUBLICATIONS

Skup, M.H. et al., *NeuroReport*, 5:1105–1109, May 1994.

*Merck Manual*, 16$^{th}$ Edition, Robert Berkow(ed.), Merck Research Laboratories, Rahway, N.J., 1992, pp. 1359–1360.

Kalcheim et al., "Neurotrophin 3 is a Mitogen for Cultured Neural Crest Cells," Proc. Natl. Acad. Sci. USA 89:1661–65 (1992).

Snider, W., "Functions of the Neurotrophins During Nervous System Development: What the Knockouts are Teaching Us," Cell 77:627–38 (1994).

Boulton et al., "ERKs: A Family of Protein–Serine/Threonine Kinases that are Activated and Tyrosine Phosphorylated in Response to Insulin and NGF," Cell 65:663–75 (1991).

Nakanishi et al., "Expression of Nerve Growth Factor Family Neurotrophins in a Mouse Osteoblastic Cell Line," Biochem. and Biophys. Res. Communications 198(3)891–97 (1994).

Kodama et al., "Establishment of a Clonal Osteogenic Cell Line from Newborn Mouse Calvaria," Jpn. J. Oral Biol. 23:899–901 (1981).

Grynkiewicz et al., "A New Generation of Ca$^{2+}$ Indicators with Greatly Improved Fluorescence Properties," J. Biol. Chem. 260(6):3440–50 (1985).

Sambrook et al., Molecular Cloning: A Laboratory Manual (2d ed., Cold Spring Harbor Laboratory Press 1989), pp. 5.61; 5.64–5.72.

Sanger et al., "DNA Sequencing with Chain–Terminating Inhibitors," Proc. Natl. Acad. Sci. USA 74(12) 5463–67 (1977).

Merlio et al., "Molecular Cloning of Rat trkC and Distribution of Cells Expressing Messenger RNAs for members of the trk Family in the Rat Central Nervous System," Neurosci. 51(3):513–32 (1992).

Lamballe et al., "trkC, a New Member of the trk Family of Tyrosine Protein Kinases, Is a Receptor for Neurotrophin–3," Cell 66:967–79 (1991).

Ikeuchi et al., "Neurotrophic Factor Family and trk Gene Products," Experimental Medicine 10(3):126–31 (1992). (with English translation).

Oshimura et al., "Chromosome Ingression by the Micronucleus Fusion Method," Biotechnology 7(2):89–92 (1989). (with English translation).

*Primary Examiner*—Anthony C. Caputa
*Assistant Examiner*—Stephen Gucker
*Attorney, Agent, or Firm*—Finnegan, Henderson, Farabow, Garrett & Dunner, L.L.P.

[57] ABSTRACT

This invention relates to a composition for metabolic bone diseaese and/or bone fractures which comprises a pharmaceutically acceptable carrier and human neurotrophin-3 (NT-3).

This invention also relates to a method for the treatment and/or prevention of metabolic bone diseaese or bone fractures which comprises administering to a patient in need of said treatment and/or prevention a medicament containing an effective amount of human neurotrophin-3 (NT-3).

10 Claims, 1 Drawing Sheet

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: -
      (B) LOCATION: 19, 23, 26
      (D) OTHER INFORMATION: /note= "N = Inosine"

(xi) SEQUENCE DESCRIPTION: SEQ ID NO:1:

GAAGCAAGGA TCAAAGATNT CTNGTNGC                         28

(2) INFORMATION FOR SEQ ID NO:2:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: -
      (B) LOCATION: 5, 20, 23, 26
      (D) OTHER INFORMATION: /note= "N = Inosine"

(xi) SEQUENCE DESCRIPTION: SEQ ID NO:2:

TCTCNCTGTC TGCCAAGCAN CCNACNCAT                        29

(2) INFORMATION FOR SEQ ID NO:3:

(i) SEQUENCE CHARACTERISTICS:

-continued

```
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 4, 16
        (D) OTHER INFORMATION: /note= "N = Inosine"

(xi) SEQUENCE DESCRIPTION: SEQ ID NO:3:

CTGNGTGGCC AGGTCNCGCG GTGCAC                                              26

(2) INFORMATION FOR SEQ ID NO:4:

(i) SEQUENCE CHARACTERISTICS:
        (A) LENGTH: 318 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

GTGAAGGCCC TGAAGGATCC CACCTTGGCT GCCAGGAAGG ATTTCCAGAG GGAGGCTGAG      60

CTGCTCACGA ACCTGCAGCA TGAGCATATT GTCAAGTTCT ATGGGGTGTG TGGTGATGGT     120

GACCCACTCA TCATGGTCTT CGAATACATG AAGCATGGAG ACCTTAACAA GTTCCTCAGG     180

GCCCATGGGC CAGATGCCAT GATCCTCGTG GATGGACAGC CAGCTCAGGC CAAGGGGGAG     240

CTAGGGCTCT CTCAGATGCT CCACATCGCC AGTCAGATAT GCTCTGGCAT GGTGTACCTG     300

GCTTCCCAGC ATTTTGTG                                                   318

(2) INFORMATION FOR SEQ ID NO:5:

(i) SEQUENCE CHARACTERISTICS:
        (A) LENGTH: 106 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Val Lys Ala Leu Lys Asp Pro Thr Leu Ala Ala Arg Lys Asp Phe Gln
 1               5                  10                  15

Arg Glu Ala Glu Leu Leu Thr Asn Leu Gln His Glu His Ile Val Lys
                20                  25                  30

Phe Tyr Gly Val Cys Gly Asp Gly Asp Pro Leu Ile Met Val Phe Glu
            35                  40                  45

Tyr Met Lys His Gly Asp Leu Asn Lys Phe Leu Arg Ala His Gly Pro
        50                  55                  60

Asp Ala Met Ile Leu Val Asp Gly Gln Pro Arg Gln Ala Lys Gly Glu
65                  70                  75                  80

Leu Cys Leu Ser Gln Met Leu His Ile Ala Ser Gln Ile Cys Ser Gly
                85                  90                  95

Met Val Tyr Leu Ala Ser Gln His Phe Val
            100                 105
```

TREATMENT METHOD OF BONE AND OSTEOBLASTS WITH NEUROTROPHIN-3 (NT-3)

BACKGROUND OF THE INVENTION

1. Field of the Invention

This invention relates to a treating and preventing agent for metabolic bone diseases containing human neurotrophin-3. Moreover, it concerns treating and preventing agent for diseases about ossification especially for bone fractures by using NT-3 as a new osteoblastic proliferative factor.

2. Description of the Prior Art

At the limited part, bone repeats ossification and bone resorption for substituting new bones for old bones to maintain endoskeleton as support function. It is also prepared to respond quickly to the change of various mechanical stresses and mineral balances. This bone reformation is carried out based on the coupling of mainly both bone resorption type cells such as osteoclasts and ossification type cells such as osteoblasts. Recently, it appears that the function of osteoblasts is not only ossification but also playing a role as a control center of cell chain reaction for bone reformation phenomenon that is closely related to the differentiation and activation of osteoclasts (Inoue, T., Mebio (1990), Special Version p.2–7).

In the bone metabolic diseases, there are such as osteoporosis, Paget's disease, osteomalacia, hyperostosis, osteopetrosis and so on. Especially, frequency of osteoporosis is very high, incidentally more than a half population of postmenopausal women and aged, and the diagnosis and effective treatment for it are strongly desired.

Bone metabolic diseases are accompanied with metabolic disorders that are specific to bones at cell level in some bone tissues. It is very effective for elucidation of these metabolic disorders to discover, separate and identify the factor that relates specifically to bone metabolism. The present inventors investigated hard to discover the specific factor of bone metabolism, and finally the present invention was accomplished.

In detail, the present inventors especially used an osteoblastic cell line which functions mainly for calcification and identified the protein produced from that cell line.

NT-3 (neurotrophin-3), presented by the present invention, is a protein discovered by Hohn, A. et al., and Maisonpierre, P. C. et al., and has an effect to promote the nerve growth. NT-3 is a protein which consists of 119 amino acid subunits dimer with Tyr on N-terminal and Thr on C-terminal, and these amino acid sequences are shown in the literature. NT-3 is available at Pepro Tech Inc., USA (Rocky Hill, N.H. 08533, USA, catalogue No. 450-03). The above mentioned literature describes the gene coding NT-3, and NT-3 can be prepared based by the method described on the literature. They were known to be four kinds of factors in the nerve growth factor family including NT-3 by now. These are nerve growth factor (NGF), brain derived neurotrophic factor (BDNF) and human neurotrophin-4, other than NT-3. The function of BDNF is to increase the number of AChE positive neuron at culture system of hippocampus, and that of NT-3 is to increase the number of calcium binding protein (Calbinin) positive neuron (Ip, N.Y. et al. J.Neurosci vol.13, P.3394–3405, 1993). Moreover, it is also reported that NT-3 increases the proliferation of precursor cells of neural crest (Kalcheim, C. et al. Proc. Natl. Acad. Sci., USA, vol.89, P.1661–1665, 1992).

On the other hand, the receptors of the NGF family are trk family and trkA, trkB, trkC are known by now (Snider, W. D. Cell vol. 77, p.627–638, 1994). NGF, BDNF and NT-3 are known to bind especially to trkA, trkB and trkC, respectively. Trk is a proto-oncogene which arises from colon cancer and has the tyrosine kinase type receptor structure including the half of C-terminal side tyrosine kinase domain. The amino acid sequence of this tyrosine kinase domain has high homology with other receptor types of tyrosine kinase. On the activity of tyrosine kinase, for example, trkA which is a receptor of NGF responded to NGF, subjected to tyrosine phosphorylation, and shows tyrosine kinase activity. By this tyrosine kinase, MAP2 (microtuble-associated protein 2, Boulton, T. G. et al. Cell vol.65, p.663–675, 1991) and phospholipase C are subjected to tyrosine phosphorylation, and consequently incorporation of calcium ion influx occurs. Proliferation signals are transmitted by this signal transmission form (Ikeuchi, T. et al., Experimental Medicine vol.10, p.126–131, 1992). By this binding of tyrosine kinase type receptor such as trkC and ligands, tyrosine kinase is activated and signal transmission is initiated. $Ca^{2+}$ channel activated by binding of ligands and receptors is called "receptor working $Ca^{2+}$ channel". It is checked in various cells such as lymphocyte, smooth muscle (Kuno, M., Experimental Medicine, vol.7, p.73–78, 1989).

It has been observed that MC3T3-E1 of the mouse osteoblast like cell line is expressing mRNA of NT-3 and the amount of mRNA can be increased by treating MC3T3-E1 cells with TGF-β (Nakanishi, et al., Biochem. Biophys. Res. Commun. vol.198, p.891–897, 1994). MC3T3-E1 is a cell line established by Kodama, H. et al., which has ability of calcification and was derived from new born mouse calvaria (Jpn. J. OralBiol. Vol. 23, p.899–901, 1981, appeared in General Catalog of RIKEN GENE BANK, No.1 April, 1995). However, no reports have been presented so far that NT-3 works as an osteoblast proliferative factor.

SUMMARY OF THE INVENTION

This invention relates to a composition for metabolic bone diseases and/or bone fractures which contains a pharmaceutically acceptable carrier and human neurotrophin-3 (NT-3).

This invention also relates to a method for the treatment and/or prevention of metabolic bone diseases or bone fractures which comprises administering to a patient in need of said treatment and/or prevention a medicament containing an effective amount of human neurotrophin-3 (NT-3).

DETAILED DESCRIPTION OF THE INVENTION

Figure 1:
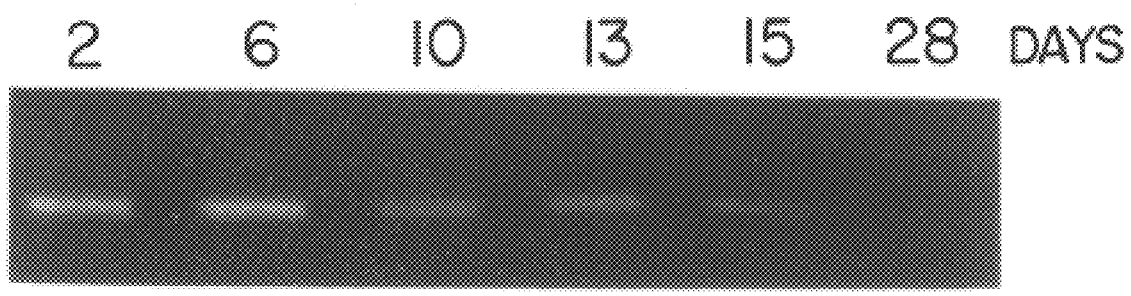
FIG. 1 is a representation of embodiment of an electrophoresis pattern of trkC.

The present inventors have newly detected that MC3T3-E1 cells express trkC with Polymerase Chain Reaction (PCR) Technology (Erich, H. A., Stochton Press Co., 1989).

Considering those detections and that trkC is a receptor of NT-3, the inventors came to a conclusion that MC3T3-E1 cells secreted NT-3 and, NT-3 proliferated themselves as autocrine. In addition, the inventors observed that the proliferation of MC3T3-E1 cells was increased and the incorporation of calcium into the cells was increased by adding NT-3 in MC3T3-E1 cell culture medium, and concluded that NT-3 worked as an osteoblast proliferative factor.

The proliferative response of MC3T3-E1 cells was detected by the cell proliferation assay kit (Amersham Co., RPN20 and RPN210). MC3T3-E1 cells were inoculated in culture dishes or 96-well microtiter plates by using inoculate of $0.5 \times 10^5$ cells/ml. Four days after the inoculation, various concentrations (0.2–100 ng/ml) of NT-3 (Pepro Tech Inc., Rocky Hill, N.H. 08553, USA, catalogue NO.450-03) were added to the cultures and proliferation was assayed by using the assay kit of Amersham Co. on the next day. The result was that NT-3 stimulated the proliferation of MC3T3-E1 cells. The ability of MC3T3-E1 cells to respond to NT-3 was further confirmed by detection of fluorescence intensity incorporation assay using a calcium sensitive fluorescent indicator. Exposure of the cells to 20–100 ng/ml of NT-3 resulted in calcium influx through their cell membrane. Moreover, incorporation of MC3T3-E1 cells progressed by NT-3 was detected by the measurement of fluoro intensity using calcium sensible fluoro agent (Grynkiewicz, G. et al. J. Biol. Chem. vol. 260, p.3440–3450, 1985). Consequently, it was confirmed that NT-3 bound to trkC and proliferated MC3T3-E1 cells by the mechanism of autocrine.

Thus, the inventors discovered that NT-3 works as an osteoblast proliferative factor. Since the osteoblast proliferative factor is an important factor for bone metabolism, the present invention is to present a preventing agent of NT-3 for bone metabolic diseases, especially for bone fractures.

This invention provides with a composition for metabolic bone diseases and/or bone fractures which contains a pharmaceutically acceptable carrier and human neurotrophin-3 (NT-3).

This invention also provides with a method for the treatment and/or prevention of metabolic bone diseases or bone fractures which comprise administering to a patient in need of said treatment and/or prevention a medicament containing an effective amount of human neurotrophin-3 (NT-3).

Medicine of the present invention can be desirably administered intravenously and intramuscularly. Phleboclysis drips as well as conventional intravenous injections are possible for administration.

Although various types for form of the medicine of the present invention can be used, it is desirable to use it as a liquid agent. For an injection agent, for example, NT-3 can be a powder agent for injection. In that case, it is added one or more than two kinds of water soluble diluents such as mannitol, sugar, milk sugar, maltose, glucose, fructose, and dissolved them in the water. After putting the mixture into vials or ampules, freeze, dry and then seal them to be an injection agent.

Although the adult clinical administration dose per day depends on how, age, weight, symptoms and so on, usually 1–500 mg is preferable for this peptide derivatives.

NT-3 presented by the present invention promotes the proliferation of MC3T3-E1 cells and calcium incorporation. So it is an effective preventing agent for bone metabolic diseases, especially for bone fractures which is related to bone formation.

The present invention is described in detail by examples written below. Though the present invention is not restricted to these examples.

EXAMPLES

Example 1

Detection of trkC

MC3T3-E1 osteoblastic cells were inoculated at a density of $0.5 \times 10^5$ cells/mi. The cells were cultured in the medium and harvested on days 2, 6, 10, 13, 15 and 28. Total RNA was isolated with guanidine isothiocyanate and phenol.

Total RNA (0.2 mg) was reverse transcribed into single-stranded cDNA with oligo d(T) using kits of Parkin Elmer, Inc./Takara Shuzo, and the single-stranded cDNA was amplified using 0.5 mM of synthetic primer oligonucleotides (Applied Biosystems, Inc.): trkf as shown in SEQ ID No.:1, trkr as shown in SEQ ID No.:2 and trkr2 as shown in SEQ ID No.:3 in the Sequence Listing. For amplification of tyrosine kinase domain of trk cDNA, primers trkf and trkr were used first using Astec PC800 (Astec Inc.) under a nonstringent condition, then the amplified solution was diluted by 50 times and the PCR products were reamplified using primers trkf and trkr2. This sample was applied by agarose gel electrophoresis and a 362-base-pair DNA fragment was detected as a trkC band as shown in FIGURE 1.

After cutting this band from the gel, DNA was extracted by using the filter kit (Takara Suptec 01 and 02, Takara Shuzo K.K). Then after DNA fragment was smoothed and phosphorylated by using Pharmacia's Clone Kit, it was inserted to dephosphorylated pUC18 vector (Sambrook, et al. Molecular Cloning A Laboratory Manual, Cold Spring Harbor Laboratory Press Co., 1989). This plasmid was transformed into *Escherichia coli* strain JM109. After isolating and culturing the colony, the plasmid was extracted by Pharmacia Flexible Prep Kit. By using this plasmid, DNA nucleic acid sequence was determined by the dideoxy method (Sanger, F. et al., Proc. Natl. Acad. Sci. USA, vol.74, p.5463–5487, 1977). When comparing the difference between the frangment of trkC of mouse determined this example (SEQ ID No:4) and (SEQ ID NO: 5) and those of rat and pig that are already known by now (Merlio, J. P. et al., Neuroscience, vol. 51, p.513–532, 1992 and Lamballe, F. et al., Cell, vol. 66, p.967–979, 1991), the different nucleic acid bases were respectively 19 and 29, the different amino acid residue was respectively 1 and 0.

Example 2

MC3T3-E1 cell proliferation assay by NT-3

The proliferative response of MC3T3-E1 cells were detected by the cell proliferation assay kit (Amersham Co., RPN20 and RPN210). MC3T3-E1 cells were inoculated in culture dishes or 96-well microtiter plates at a density of $0.5 \times 10^5$ cells/mi. Four days after the inoculation, various concentrations (0.2–100 ng/ml) of NT-3 (Pepro Tech Inc., Rocky Hill, N.H. 08553, USA, catalogue No.450-03) were added to the cultures and proliferation was assayed by using the assay kit of Amersham Co. on the next day. In this kit, bromodeoxyuridine BrdU is incorporated into DNA of cells. After binding to mouse anti-BrdU antibody, BrdU was detected by peroxidase activity using anti-mouse antibody binding the second antibody conjugated with peroxidase. The results are shown in Table 1. Those values are relative activity indicating 1.0 when the concentration is 0 ng/ml.

TABLE 1

| Concentration (ng/ml) | 0 | 0.2 | 1 | 5 | 20 | 100 |
|---|---|---|---|---|---|---|
| NT-3 | 1.0 | 1.07 | 1.14 | 1.34 | 1.63 | 1.44 |

Example 3

Calcium incorporation assay

Total volume of 1.5 ml of MC3T-E1 cells were inoculated in culture dishes of 25 mm diameter at a density of $7.5 \times 10^4$ cells/ml in 5% of fetal bovine serum/α-MEN (Gibco Co.) including various concentration of NT-3. One day after the inoculation and washing twice with PBS, 5 mM Fura-2AM (Dojin Co.) dissolved in HEPES buffer (132 mM NaCl, 35 mM KCl, 0.5 mM $MgCl_2$, 1 mM $CaCl_2$, 9.5 mM HEPES, 5 mM Glucose, pH 7.4) was treated for 30 min at room temperature. After washing the cells, the absorbance ratio at 340 nm/380 nm was measured, and the relative ratio indicating 1 when treating 0.05 ng/ml of NT-3. The results are shown in Table 2.

TABLE 2

| NT-3 (ng/ml) | 0.05 | 0.2 | 1.0 | 5.0 | 20 |
|---|---|---|---|---|---|
| NT-3 | 1 | 1 | 1.13 | 1.25 | 1.69 |

It was proved that calcium incorporation occurred when adding NT-3 to the culture. It can be considered that the signal, transmitted by trkC which is a receptor, activated $Ca^{2+}$ channel and resulted in as calcium influx.

What is claimed is:

1. A method for the treatment of bone fractures which comprises administering to a patient in need of said treatment a pharmaceutical composition containing, as an active ingredient, an effective amount of isolated human neurotrophin-3.

2. The method for treating bone fractures as claimed in claim 1, wherein the effective amount is from 1–500 mg/kg/day.

3. A method for the treatment of metabolic bone diseases which comprises, administering to a patient in need of said treatment a pharmaceutical composition containing, as an active ingredient, an effective amount of isolated human neurotrophin-3.

4. The method for treating metabolic bone diseases as claimed in claim 3, wherein the effective amount is from 1–500 mg/kg/day.

5. A method for the treatment of osteoporosis which comprises, administering to a patient in need of said treatment a pharmaceutical composition containing, as an active ingredient, an effective amount of isolated human neurotrophin-3.

6. The method for treating osteoporosis as claimed in claim 5, wherein the effective amount is from 1–500 mg/kg/day.

7. A method of stimulating the proliferation of osteoblasts comprising administering a composition containing, as an active ingredient, an effective amount of isolated human neurotrophin-3.

8. The method of stimulating the proliferation of osteoblasts as claimed in claim 7, wherein the composition is a pharmaceutical composition administered to a patient.

9. The method of stimulating the proliferation of osteoblasts as claimed in claim 8, wherein from 1–500 mg of neurotrophin-3/kg/day is administered to a patient.

10. The method of stimulating the proliferation of osteoblasts as claimed in claim 7, wherein osteoblasts are exposed to 20–100 ng/ml of neurotrophin-3.

* * * * *